United States Patent
Brosio et al.

(10) Patent No.: US 10,288,591 B2
(45) Date of Patent: May 14, 2019

(54) EXHAUST SENSOR FOR INTERNAL COMBUSTION ENGINES

(71) Applicant: GM GLOBAL TECHNOLOGY OPERATIONS LLC, Detroit, MI (US)

(72) Inventors: Fulvio Brosio, Turin (IT); Luca Giuseppe Pairolero, Cascine Vica Rivoli (IT); Carlo Daniele Ceriani, Turin (IT)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 122 days.

(21) Appl. No.: 15/371,828

(22) Filed: Dec. 7, 2016

(65) Prior Publication Data

US 2017/0160249 A1 Jun. 8, 2017

(30) Foreign Application Priority Data

Dec. 8, 2015 (GB) .................................. 1521621.1

(51) Int. Cl.
| | | |
|---|---|---|
| *G01N 33/00* | (2006.01) | |
| *G01N 27/407* | (2006.01) | |
| *F01N 13/00* | (2010.01) | |
| *H05B 3/10* | (2006.01) | |
| *H05B 3/46* | (2006.01) | |

(52) U.S. Cl.
CPC ....... *G01N 33/0029* (2013.01); *F01N 13/008* (2013.01); *G01N 27/4077* (2013.01); *H05B 3/10* (2013.01); *H05B 3/46* (2013.01); *F01N 2560/02* (2013.01); *F01N 2560/20* (2013.01)

(58) Field of Classification Search
CPC ........... G01N 33/0029; G01N 27/4077; G01N 27/4067; H05B 3/10; F01N 13/008; F01N 2560/02; F01N 2560/20
See application file for complete search history.

(56) References Cited

U.S. PATENT DOCUMENTS

| | | | | |
|---|---|---|---|---|
| 4,212,273 A | * | 7/1980 | Maruoka | F02D 41/144 |
| | | | | 123/438 |
| 4,784,728 A | * | 11/1988 | Capone | G01N 27/4067 |
| | | | | 204/408 |
| 6,120,664 A | * | 9/2000 | Patel | G01N 27/4077 |
| | | | | 204/424 |
| 6,182,498 B1 | * | 2/2001 | Mizutani | G01N 27/4077 |
| | | | | 123/691 |

(Continued)

FOREIGN PATENT DOCUMENTS

| | | |
|---|---|---|
| EP | 2009435 A1 | 12/2008 |
| JP | H01253575 A | 10/1989 |
| JP | H10206374 A | 8/1998 |

OTHER PUBLICATIONS

Great Britain Patent Office, Great Britain Search Report for Great Britain Application No. 1521621.1, dated Apr. 14, 2016.

*Primary Examiner* — Freddie Kirkland, III
(74) *Attorney, Agent, or Firm* — Lorenz & Kopf, LLP

(57) ABSTRACT

A sensor for exhaust gases of an internal combustion engine includes a sensing element enclosed in a sensor housing. The sensor housing includes a protective cap having a plurality of openings formed therein for allowing flow of exhaust gases through the protective cap towards the sensing element. The sensor further includes at least one heating element for burning exhaust gas deposits on the sensor.

20 Claims, 4 Drawing Sheets

(56) References Cited

U.S. PATENT DOCUMENTS

| | | | | |
|---|---|---|---|---|
| 6,691,553 B2* | 2/2004 | Holleboom | ............ | G01D 11/245 |
| | | | | 73/23.32 |
| 7,850,833 B2* | 12/2010 | Aoki | .................. | G01N 27/4077 |
| | | | | 123/406.23 |
| 9,395,325 B2* | 7/2016 | Isomura | ............. | G01N 27/4067 |
| 9,732,660 B2* | 8/2017 | Di Perna | ............... | F01N 3/2006 |
| 9,733,208 B2* | 8/2017 | Isomura | ............... | G01N 27/409 |
| 2008/0223110 A1* | 9/2008 | Weyl | ................. | G01N 27/4077 |
| | | | | 73/31.05 |
| 2013/0334043 A1* | 12/2013 | Isomura | ............. | G01N 27/4067 |
| | | | | 204/424 |
| 2014/0144777 A1* | 5/2014 | Isomura | ............... | G01N 27/409 |
| | | | | 204/408 |
| 2017/0152786 A1* | 6/2017 | Di Perna | ............... | F01N 3/2006 |

* cited by examiner

EXHAUST SENSOR FOR INTERNAL COMBUSTION ENGINES

CROSS-REFERENCE TO RELATED APPLICATION

This application claims priority to Great Britain Patent Application No. 1521621.1, filed Dec. 8, 2015, which is incorporated herein by reference in its entirety.

TECHNICAL FIELD

The present disclosure pertains to a sensor for monitoring exhaust gases, e.g. for detecting the composition of exhaust gases. The disclosure relates more specifically to sensors or probes (e.g. $NO_x$ sensors, lambda sensors, pressure sensors, temperature sensors, etc.) including a sensing element configured to be exposed to exhaust gases produced by internal combustion engines (e.g. Diesel engines).

BACKGROUND

Internal combustion engines may be provided with sensors for monitoring exhaust gases. Generally, sensors are provided with a sensing element located within a sensor housing intended to be exposed to exhaust gases. Typically, sensors are arranged at the exhaust pipes of an exhaust system by screwing the end portion of the sensor in a threaded bore provided on the exhaust pipe. As a result, the sensing element is exposed to exhaust gases so that sensors can collect exhaust gas data such as temperature, pressure, chemical composition, etc. of the exhaust gases.

Exhaust gas data can be useful for controlling emissions and to improve the efficiency of the engine. For example, sensors like Lambda sensors or oxygen ($O_2$) sensors can be used for closed looped control of the fuel quantity to be injected by injectors to obtain an optimal air/fuel ratio. Such sensors are provided with a sensing element (typically a ceramic element) for detecting the residual oxygen in the exhaust gases. In this way, a precise indication of whether combustion is complete or not is given by the exhaust gas sensor, allowing to improve the efficiency of combustion and to reduce the amounts of both unburnt fuel and nitrogen oxides ($NO_x$) entering the atmosphere. In other words, by monitoring the composition of exhaust gases (e.g. by detecting the residual oxygen in exhaust gases), it is possible to determine if the air/fuel mixture during the combustion was rich or lean and based on this information the air/fuel ratio can be adjusted to obtain an optimal value (in most cases close to stoichiometric).

Normally, the sensing element is arranged in a sensor housing provided with a protective cap (or protective tube) for providing a mechanical protection for the sensing element during shipping. The protective cap is also provided with openings designed to allow gas contact with the sensing element.

During the operation of an internal combustion engine, exhaust products (soot, unburned hydrocarbons, ashes, etc.) are generated which can flow through the exhaust pipe line. As a result, exhaust gas deposit can accumulate so as to partially, or completely, covering the protective cap and/or obstruct the related openings. In this condition the functionality of the exhaust gas sensor (accuracy, response time) is limited or null. Replacement or maintenance of the exhaust gas sensor is thus needed, with consequent waste of time and money.

Furthermore, some exhaust gas sensors (e.g. Lambda sensors) are provided with a sensing element that must be heated up to an operative temperature. In these sensors, a heater is integrated in the sensing element. Thus, after an engine cold start, the sensing element is ready to operate after a time period called "light-off time" during which the sensing element reaches the operating temperature. In some cases, the light-off time can be very long due to the presence of condensed water inside the protective cap. In particular, in order to avoid the contact of condensed water with the hot sensing element, which may damage the sensor and lead to failure, the sensing element is heated slowly, or it is not heated, when the engine is cold. The sensing element reaches the operative temperature and starts its operation only when exhaust gases reach the end of the dew point, so that condensed water is completed removed from the exhaust gas.

During the light-off time, signals coming from exhaust gas sensors cannot be used for regulating the engine operating values (e.g. the air/fuel ratio) and thus only an open loop control can be provided based on predetermined values stored in a map. In this situation, emissions and efficiency of the engine are not optimal.

SUMMARY

In accordance with one aspect of the present disclosure, an exhaust gas sensor is provided which has a reliability and a life span greater than the conventional exhaust gas sensors and with a reduced light-off time. The present disclosure further provides an internal combustion engine which is reliable, efficient and causing reduced emissions also during engine cold start operations.

In accordance with another aspect of the present disclosure a method is provided for removing deposits from the protective cap of an exhaust gas sensor without disassembling the exhaust gas sensor from the exhaust system. These aspects of the present disclosure are accomplished with a simple, rational and rather inexpensive solution.

An embodiment of the present disclosure provides for a sensor for exhaust gases of an internal combustion engine having a sensing element enclosed in a sensor housing. The sensor housing includes a protective cap having a plurality of openings for allowing flow of exhaust gases through the protective cap towards the sensing element. The exhaust gas sensor further includes at least one burning or heating element for burning exhaust gas deposits such as soot, unburned hydrocarbons, ashes, etc. formed on the protective cap.

Advantageously, the heating element burns deposits of exhaust product on the protective cap. In this way, exhaust gas deposits can be removed from the protective cap and in particular from the above-mentioned openings. As a result, the reliability and the life span of the exhaust gas sensor can be improved.

According to aspects of the present disclosure, the heating element may be arranged on the internal surface of the protective cap and/or arranged on the external surface of the protective cap. As a result, exhaust gas deposits are burned on the protective cap in a simple and reliable manner.

According to an aspect of the present disclosure, the exhaust gas sensor includes an internal element arranged within the protective cap and a heating element is arranged on the internal element. The heating element can be arranged on the internal surface of the internal element and/or on the external surface of the internal element.

The internal element may be configured so as provide an internal cap arranged within the protective cap of the exhaust gas sensor. A heating element arranged on an internal element of the exhaust gas sensor, e.g. an internal cap, effectively burns exhaust gas deposits.

According to still another aspect of the present disclosure, the heating element includes an electrical heater. As a result, the heating element can be operated and controlled in a reliable manner.

According to a particular aspect of the present disclosure, the heating element includes at least one resistor. Such a heating element has proven to be a simple, reliable and cost-effective component.

According to another aspect of the present disclosure, the heating element includes a supporting layer having at least one resistor being fixed thereon. As a result, the heating element can be coupled to the protective cap and/or to the internal element (e.g. an internal cap) in a simple manner and the supporting layer can be constrained in an easier way to the cap or the internal element.

According to a particular aspect of the present disclosure, the supporting layer is made of a thermal conductive material. Thanks to this aspect, the heat generated by at least one resistor is transferred to the protective cap uniformly.

According to a particular aspect of the present disclosure, the supporting layer is made of steel. This aspect allows heating the protective cap to a temperature of up to 1000° C.

According to a particular aspect of the present disclosure, the heating element includes a thick film heater. This aspect allows providing the heating element on the protective cap and/or on the internal element (e.g. an internal cap) without affecting the general design of the exhaust gas sensor.

According to still another aspect of the present disclosure, the heating element is configured to heat the protective cap to a temperature greater than 600° C., i.e. a temperature that allows removal of exhaust gas deposits, which is also referred to herein as "self-cleaning temperature." This aspect allows quickly and reliably removing exhaust gas deposits from the protective cap.

Another embodiment of the present disclosure provides for an internal combustion engine including an exhaust system having at least one exhaust gas sensor according to one or more of the preceding aspects.

With the exhaust gas sensor, it is possible to improve the reliability of an internal combustion engine. In particular, exhaust products that deposit on the protective cap of the exhaust gas sensor are burned, and thus removed by the heating element. This aspect allows cleaning exhaust gas sensor(s) of the internal combustion engine without overhauling or replacement at a dealer.

Another embodiment of the present disclosure provides for a method for removing exhaust gas deposits from the protective cap of an exhaust gas sensor by activating at least one heating element to burn the exhaust gas deposits. Advantageously, the heating element heats the protective cap of the exhaust gas sensor up to burn off deposits of exhaust products from the protective cap of the exhaust gas sensor. This aspect cleans the exhaust gas sensor without the need of disassembling it from the exhaust pipe to which it is fastened.

According to a particular aspect of the present disclosure, the protective cap is heated to a temperature greater than 600° C. As mentioned above, this aspect allows to remove quickly and reliably deposits of exhaust products from the protective cap.

According to still another aspect of the present disclosure, the protective cap is heated during an engine cold start. As a result, the light-off time of the exhaust gas sensor is reduced. In particular, during an engine cold start, the protective cap is heated at least up to a temperature that allows to quickly evaporate the possible water condensed into the protective cap. Thus, the sensing element can reach the operative temperature in a reduced light-off time, without the risk of thermal shocks. Furthermore, the heat generated by the heating element can used to pre-heat the sensing element that reduces the energy consumption for heating the sensing element. As a result, it is possible to improve efficiency and emissions of an internal combustion engine also during engine cold start operations.

BRIEF DESCRIPTION OF THE DRAWINGS

The present disclosure will hereinafter be described in conjunction with the following drawing figures, wherein like numerals denote like elements.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

Figure 1:
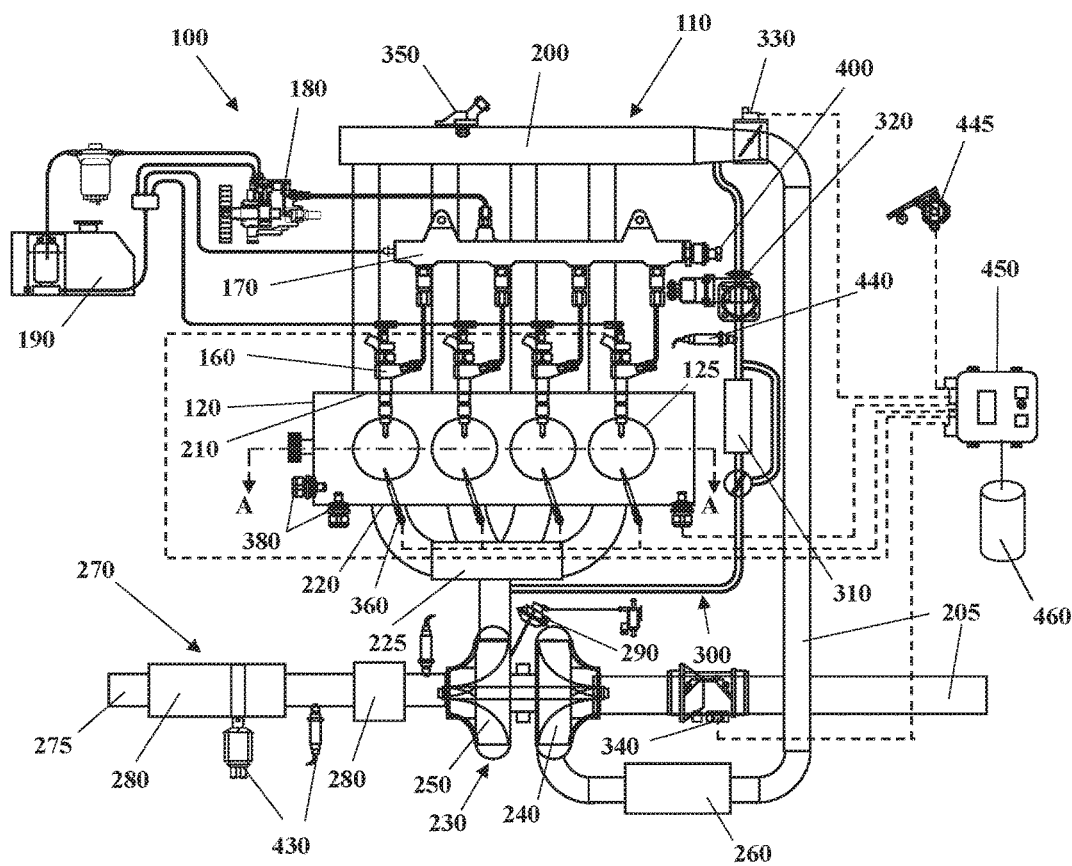
FIG. 1 schematically shows an automotive system belonging to a motor vehicle.
Figure 2:
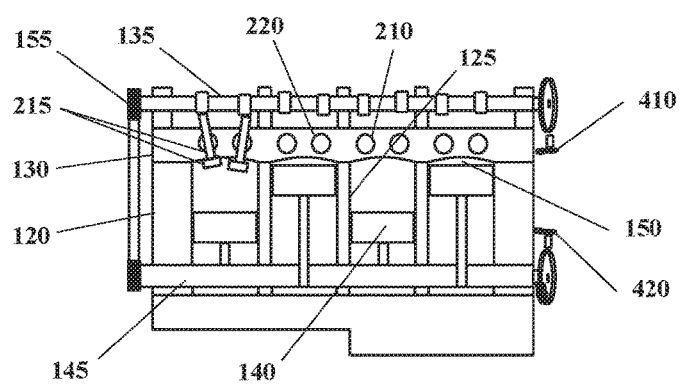
FIG. 2 is the section A-A of an internal combustion engine belonging to the automotive system of FIG. 1.

Some embodiments may include an automotive system 100, as shown in FIGS. 1 and 2, that includes an internal combustion engine (ICE) 110 having an engine block 120 defining at least one cylinder 125 having a piston 140 coupled to rotate a crankshaft 145. A cylinder head 130 cooperates with the piston 140 to define a combustion chamber 150.

A fuel and air mixture (not shown) is disposed in the combustion chamber 150 and ignited, resulting in hot expanding exhaust gasses causing reciprocal movement of the piston 140.

The fuel is provided by at least one fuel injector 160 and the air through at least one intake port 210. The fuel is provided at high pressure to the fuel injector 160 from a fuel rail 170 in fluid communication with a high-pressure fuel pump 180 that increase the pressure of the fuel received from a fuel source 190. Each of the cylinders 125 has at least two valves 215, actuated by a camshaft 135 rotating in time with the crankshaft 145. The valves 215 selectively allow air into the combustion chamber 150 from the port 210 and alternately allow exhaust gases to exit through a port 220. In some examples, a cam phaser 155 may selectively vary the timing between the camshaft 135 and the crankshaft 145.

The air may be distributed to the air intake port(s) 210 through an intake manifold 200. An air intake duct 205 may provide air from the ambient environment to the intake manifold 200. In other embodiments, a throttle body 330 may be provided to regulate the flow of air into the manifold 200. In still other embodiments, a forced air system such as a turbocharger 230, having a compressor 240 rotationally coupled to a turbine 250, may be provided. Rotation of the compressor 240 increases the pressure and temperature of the air in the duct 205 and manifold 200. An intercooler 260 disposed in the duct 205 may reduce the temperature of the air. The turbine 250 rotates by receiving exhaust gases from an exhaust manifold 225 that directs exhaust gases from the exhaust ports 220 and through a series of vanes prior to expansion through the turbine 250. This example shows a variable geometry turbine (VGT) with a VGT actuator 290 arranged to move the vanes to alter the flow of the exhaust gases through the turbine 250. In other embodiments, the turbocharger 230 may be fixed geometry and/or include a waste gate.

The exhaust gases exit the turbine 250 and are directed into an exhaust system 270. The exhaust system 270 may include an exhaust pipe 275 having one or more exhaust aftertreatment devices 280. The aftertreatment devices may be any device configured to change the composition of the exhaust gases. Some examples of aftertreatment devices 280 include, but are not limited to, catalytic converters (two and three way), oxidation catalysts, lean NOx traps, hydrocarbon adsorbers, selective catalytic reduction (SCR) systems, and particulate filters. Other embodiments may include an exhaust gas recirculation (EGR) system 300 coupled between the exhaust manifold 225 and the intake manifold 200. The EGR system 300 may include an EGR cooler 310 to reduce the temperature of the exhaust gases in the EGR system 300. An EGR valve 320 regulates a flow of exhaust gases in the EGR system 300.

The automotive system 100 may further include an electronic control unit (ECU) 450 in communication with one or more sensors and/or devices associated with the ICE 110. The ECU 450 may receive input signals from various sensors configured to generate the signals in proportion to various physical parameters associated with the ICE 110. The sensors include, but are not limited to, a mass airflow and temperature sensor 340, a manifold pressure and temperature sensor 350, a combustion pressure sensor 360, coolant and oil temperature and level sensors 380, a fuel rail pressure sensor 400, a cam position sensor 410, a crank position sensor 420, exhaust gas sensors 430 for detecting e.g. temperature, pressure, composition of exhaust gases, an EGR temperature sensor 440, and an accelerator pedal position sensor 445. Furthermore, the ECU 450 may generate output signals to various control devices that are arranged to control the operation of the ICE 110, including, but not limited to, the fuel injectors 160, the throttle body 330, the EGR valve 320, the VGT actuator 290, and cam phaser 155. Note, dashed lines are used to indicate communication between the ECU 450 and the various sensors and devices, but some are omitted for clarity.

Turning now to the ECU 450, this apparatus may include a digital central processing unit (CPU) in communication with a memory system and an interface bus. The CPU is configured to execute instructions stored as a program in the memory system 460, and send and receive signals to/from the interface bus. The memory system 460 may include various storage types including optical storage, magnetic storage, solid state storage, and other non-volatile memory. The interface bus may be configured to send, receive, and modulate analog and/or digital signals to/from the various sensors and control devices.

The program may embody the methods disclosed herein, allowing the CPU to carryout out the steps of such methods and control the ICE 110.

The program stored in the memory system 460 is transmitted from outside via a cable or in a wireless fashion. Outside the automotive system 100 it is normally visible as a computer program product, which is also called computer readable medium or machine readable medium in the art, and which should be understood to be a computer program code residing on a carrier, the carrier being transitory or non-transitory in nature with the consequence that the computer program product can be regarded to be transitory or non-transitory in nature.

An example of a transitory computer program product is a signal, e.g. an electromagnetic signal such as an optical signal, which is a transitory carrier for the computer program code. Carrying such computer program code can be achieved by modulating the signal by a conventional modulation technique such as QPSK for digital data, such that binary data representing the computer program code is impressed on the transitory electromagnetic signal. Such signals are e.g. made use of when transmitting computer program code in a wireless fashion via a WiFi connection to a laptop.

In case of a non-transitory computer program product the computer program code is embodied in a tangible storage medium. The storage medium is then the non-transitory carrier mentioned above, such that the computer program code is permanently or non-permanently stored in a retrievable way in or on this storage medium. The storage medium can be of conventional type known in computer technology such as a flash memory, an Asic, a CD or the like.

Figure 3:
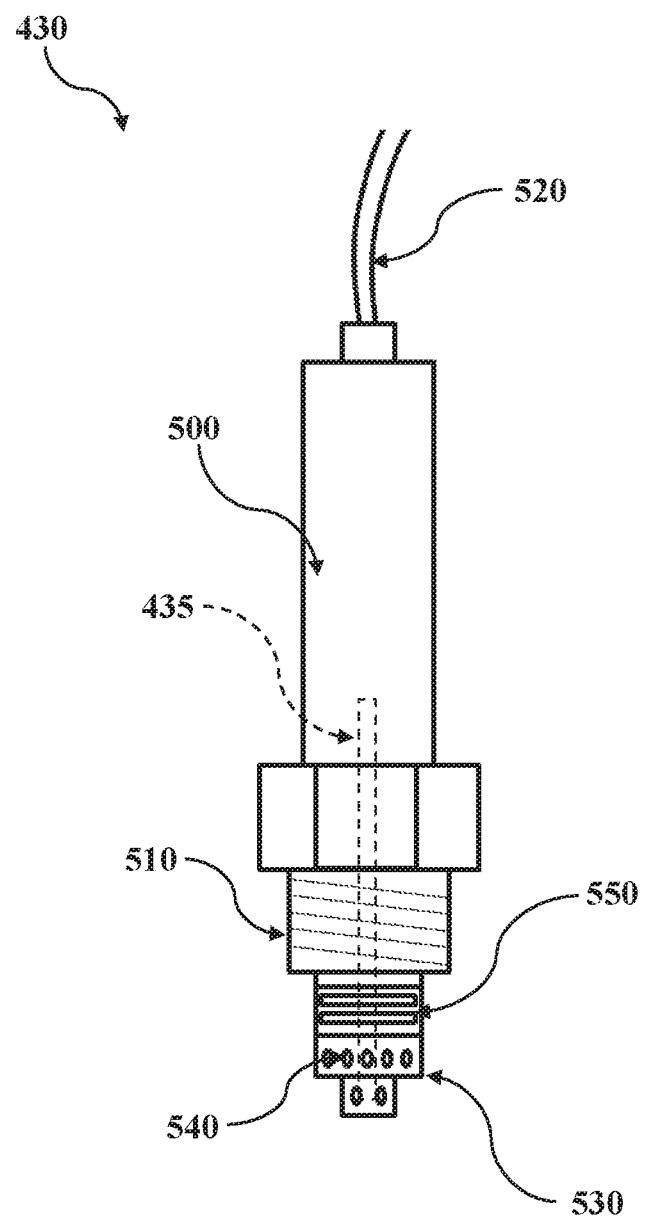
FIG. 3 shows an exhaust gas sensor according to an embodiment of the present disclosure.

With reference to FIG. 3, an embodiment of an exhaust gas sensor will be now discussed. FIG. 3 shows an exhaust gas sensor 430 including a sensing element 435 (shown in dotted line) enclosed in a sensor housing 500. The sensor housing 500 is preferably provided with a threaded end portion 510 configured to be screwed in a threated bore provided in an exhaust pipe 275. In this way, the exhaust gas sensor 430 can be tightly fastened to an exhaust pipe 275. The sensing element 435 protrudes from the threaded end portion 510 so that when the exhaust gas sensor 430 is fastened to the exhaust pipe 275, the sensing element 435 is exposed to the exhaust gases flowing inside the exhaust pipe 275.

For example, the exhaust gas sensor 430 can be provided with a sensing element 435 made of a ceramic material (e.g. zirconium dioxide, titanium dioxide) for detecting the residual oxygen in the exhaust gases. In this case the exhaust gas sensor 430 is an $O_2$ sensor (also known as Lambda sensor). Another embodiment of the present disclosure can provide that the exhaust gas sensor 430 is a $NO_x$ sensor for measuring the concentration of nitrogen oxides in exhaust gases. Thanks to the sensing element 435 provided on the exhaust gas sensor 430, various data of the exhaust gases (e.g. temperature and/or pressure and/or composition, etc.) can be measured by the exhaust gas sensor 430. In general, the exhaust gas sensor 430 includes a sensing element 435 configured to be exposed to exhaust gases. Preferably, the electrical signals produced by the sensing element can be sent to the ECU 450 by electrical cables 520 coming out from an end of the sensor housing 500.

The sensor housing 500 includes a protective cap 530 enclosing the portion of sensing element 435 protruding from the threaded end portion 510 of the sensor housing 500. The protective cap 530 has a plurality of openings 540 allowing flow of exhaust gases towards the sensing element. Openings 540 allow contact between the sensing element 435 and the exhaust gas.

The exhaust gas sensor 430 may be provided with one or more internal element 580 arranged within the protective cap 530, as for example shown in the embodiment of FIG.

5. The internal element 580 can be provided with openings 540*a* allowing flow of exhaust gases towards the sensing element 435. In general, one or more internal element 580 are configured to provide a labyrinth shape, and thus a labyrinth path for the exhaust gases within the protective cap 530. The labyrinth path provided by the at least one internal element 580 allows avoid that condensed water contact the sensing element 430.

According to various embodiments, the internal element 580 can includes one or more walls arranged within the protective cap 530.

Figure 5:
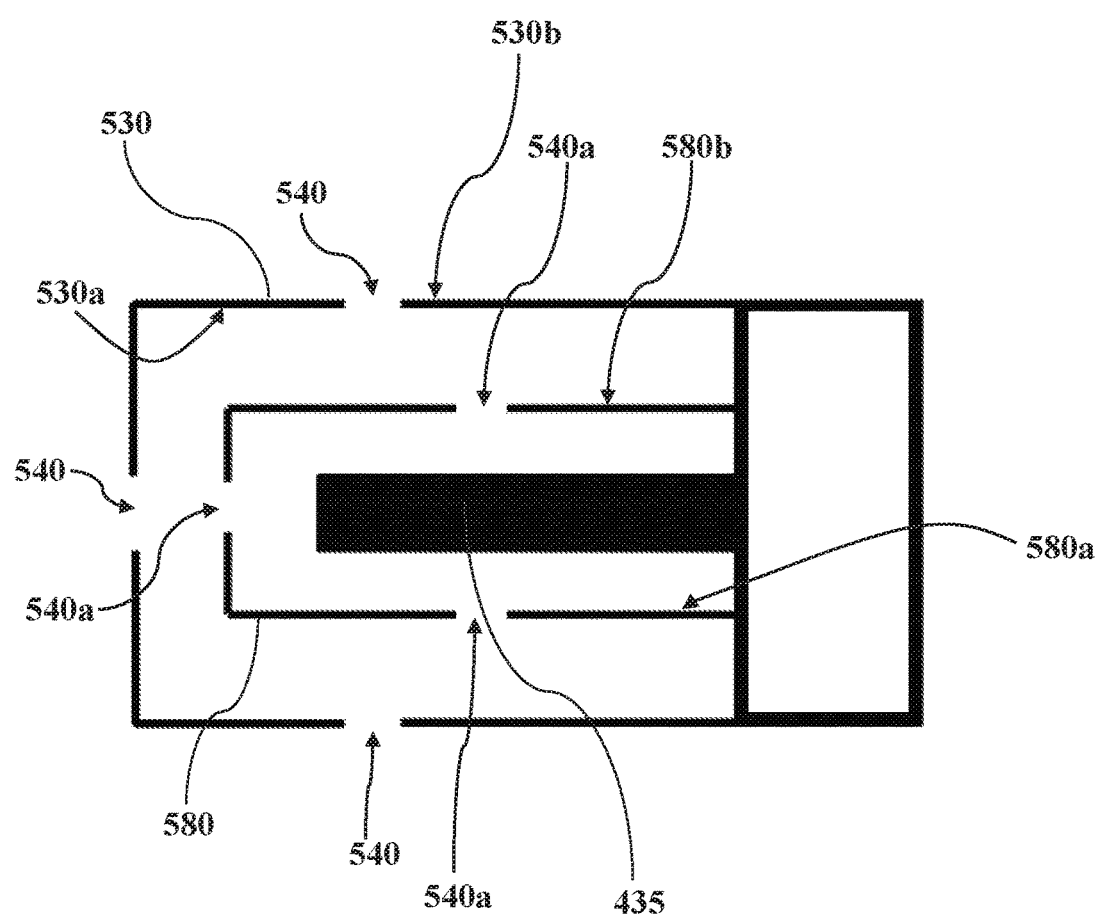
FIG. 5 is a schematic section view of an embodiment of a protective cap including an internal element.

According to an embodiment, as for example shown in FIG. 5, the internal element 580 is configured to form an internal cap, that is arranged inside the protective cap 530, preferably coaxially with the protective cap 530. In other words, the sensing element 435 can be arranged inside an internal cap 580, which is in turn arranged inside the protective (external) cap 530.

When the threaded portion 510 of the sensor housing 500 is screwed in the exhaust pipe 275, the protective cap 530 is located inside the pipe 275 and the sensing element 435 can be exposed to exhaust gases thanks to the openings 540 (540*a* if the sensor is provided with one or more internal cap) which allow the exhaust gases to flow towards the sensing element 435.

The exhaust gas sensor 430 includes at least one burning or heating element 550 configured for burning exhaust gas deposits on the protective cap 530. As mentioned above, during the operation of an internal combustion engine 110, exhaust gas deposits (soot, unburned hydrocarbons, ashes, etc.) can be generated and thus deposit on the protective cap 530. As a result, exhaust gas deposits can cover the openings 540 so as to prevent exhaust gases from flowing through the protective cap 530 and from reaching the sensing element 435 of the exhaust gas sensor. Thanks to the heating element 550, exhaust gas deposits are burned and thus removed from the protective cap 530. In this way, openings 540 are freed from exhaust deposits and the exhaust gas sensor 430 can operate for a prolonged time.

Figure 4:
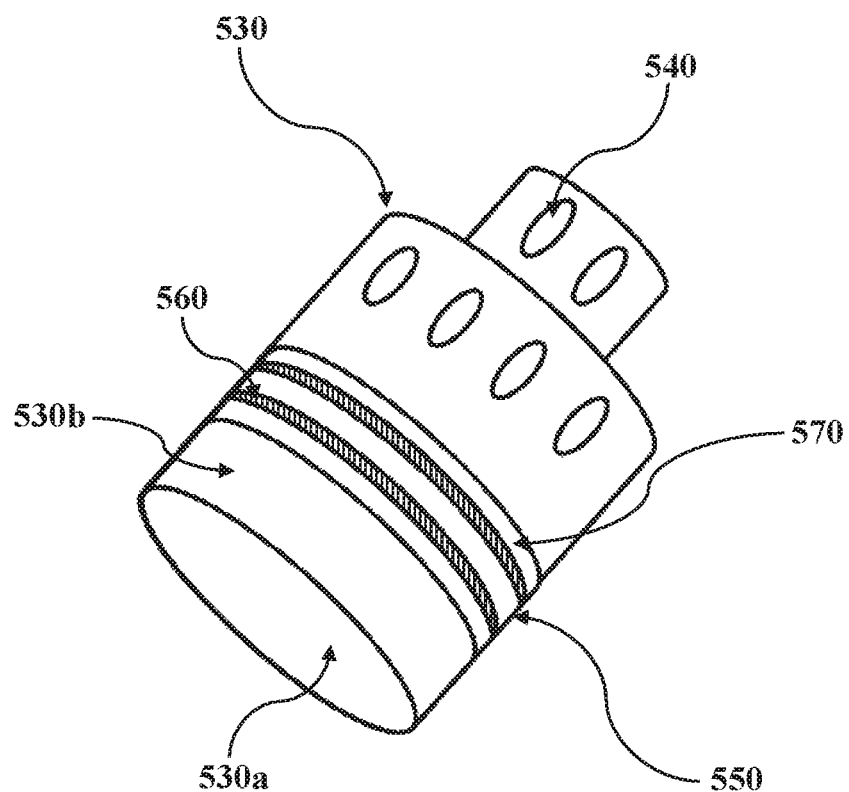
FIG. 4 shows the protective cap of the exhaust gas sensor shown in FIG. 3.

FIG. 4 shows the protective cap 530 of the exhaust gas sensor 430 of FIG. 3. The protective cap 530 has a substantially tubular shape with an internal surface 530*a* (facing the sensing element in operative condition) and an external surface 530*b,* opposite to the internal surface 530*a.*

In the shown embodiment, the heating element 550 is arranged on the external surface 530*b* of the protective cap 530. Further embodiments can provide that the heating element 550 is arranged on the internal surface 530*a* of the protective cap, or can provide that one or more heating element is arranged on the external surface 530*b* of the protective cup and one or more heating element 550 is arranged on the internal surface 530*a* of the protective cap 530.

As already mentioned above, the exhaust gas sensor 430 can include at least one internal element 580 arranged within protective cap 530, for example to form an internal protective cap (see for example the schematic section view of the embodiment of FIG. 5). At least one heating element 550 can be arranged on the internal element 580. The arrangement of the heating element 550 on the protective cap 530 may also be applied to the arrangement of the heating element 550 on the internal element 580 of the exhaust gas sensor 430, e.g. on one or more internal cap.

For example, according to various embodiments, at least one heating element 550 can arranged on the internal surface 580*a* of the internal element 580, and/or at least one heating element 550 can be arranged on the external surface 580*b* of the internal element 550. Preferably, the heating element 550 includes an electrical heater. More preferably, the heating element 550 includes at least one resistor 560 configured to generate heat by Joule effect.

In the embodiment shown in FIG. 4, the heating element 550 is provided with two resistors 560, preferably arranged around the external surface 530*b* of the protective cap 530. Resistors 560 are configured to be electrically connected to an electrical power source (e.g. an automotive battery or an auxiliary battery), preferably by electric wires 520. By supplying an electrical current to the resistors 560, heat can be generated by Joule effect and the protective cap is heated for burning exhaust gas deposits.

Further embodiments can provide a different number of resistors 560. For example, an embodiment can provide that the heating element 550 has a single resistor 560 (or a plurality of resistors 560 connected in series). Another embodiment can provide for example that the heating element 550 is provided with a number of resistors 560 greater than two, connected in parallel to each other. In general, the heating element 550 includes at least one resistor 560.

Preferably, the heating element 550 includes a supporting layer 570, preferably made of a thermal conductive material. Resistors 560 can be fixed to the supporting layer 570 for example by welding and/or by a conductive paste. In a preferred embodiment resistors 560 are deposited on the supporting layer 570 by a thick film technology (e.g. by a screen printing process). Thick film technology provides a heating element 550 in the form of a thick film heater that can be attached to the protective cap 530 and/or on the internal element(s) 580 (e.g. one or more internal cap) in a simple manner without affecting the general design of the exhaust gas sensor 430.

The embodiment shown in FIG. 4 is provided with a heating element 550 having a supporting layer 570 arranged on the external surface 530*b* of the protective cap 530. As discussed above, further embodiments can provide that the supporting layer 570 of the heating element 550 is arranged on the internal surface 530*a* of the protective cap 530. In this configuration, resistors 560 are located inside the protective cap 530, preferably faced towards the sensing element 435. As mentioned, the supporting layer 570 is preferably made of a thermal conductive material so as to allow to transfer the heat generated by resistors 560 to the protective cap 530 uniformly.

Preferably the supporting layer 570 is made of steel (e.g. stainless steel, preferably stainless steel 300 grades) or a nickel-chromium-based alloys (e.g. Inconel). In a preferred embodiment, the supporting layer 570 is made of the same material of which is made the protective cap 530. Thanks to supporting layer made of steel, the heating element 550 can heat the protective cap up to 1000° C. In general, the heating element 550 of the present disclosure is configured to heat the protective cap 530 above a temperature greater than 600° C. Above this temperature, deposits of exhaust product on the protective cap 530 are burned and thus removed from the protective cap 530 in a reliable manner avoiding the risk of occlusion of the openings 540.

An alternative embodiment can provide that the supporting layer 570 is absent. In this case a portion of the protective cap 530 and/or the internal element(s) 580 (e.g. one or more internal cap) can act as a supporting layer. In other words, resistors 560 can be fixed directly on the internal surface 530*a* and/or on the external surface 530*b* of the protective cap 530. As mentioned above, resistors 560 can be fixed directly on the internal surface 580*a* and/or on the external surface 580*b* internal element(s) 580 (e.g. one or more internal cap). For example, an embodiment of the present disclosure can provide that one or more resistors 560 are fixed to the protective cap 530 of the exhaust gas sensor 430, for example by using a screen printing process. In this embodiment resistors 560 can be fixed to the protective cap 530 during the production of the protective cap 530.

From the foregoing, one skilled in the art will appreciate that different methods and technologies of providing the resistor on a surface of the protective cap 530 and/or of the internal element 580 may be used.

In accordance with the present disclosure, the protective cap 530 of the exhaust gas sensor 430 can be cleaned without the need of disassembling the exhaust gas sensor 430 from the exhaust pipe 275. In particular, by heating the protective cap 530 by means of the heating element 550, deposits of exhaust products are burned and removed from the protective cap 530. Operation of the heating element 550 is preferably carried out periodically according to the needs, for example according to the detection of exhaust deposits (exhaust soot) quantity present on the protective cap, or according to a predetermined period (which can be for example stored in the ECU).

In this way reliability and life span of exhaust gas sensors 430 are improved. Furthermore, by carrying out the step of heating the protective cap 530 during an engine cold start, if condensed water is present inside the protective cap 530, it can be evaporated quickly. In this way, the sensing element 435 can be heated up to the operative temperature in a safe manner without any risk of thermal shocks due to contact between the hot sensing element and condensed water present in the protective cap 530. Furthermore, during the step of heating the protective cap 530, the sensing element 435 is pre-heated by the heat generated by the heating element 550. As a result, the sensing element 435 can be heated up to the operative temperature in a reduced light-off time. Energy consumption is reduced as well. In this way, efficiency and emissions of an internal combustion engine 110 can be improved also during engine cold start operations.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. A sensor for exhaust gases of an internal combustion engine, comprising:
    a sensor housing including a protective cap having a plurality of openings for allowing a flow of exhaust gases through said protective cap;
    a sensing element enclosed in a sensor housing such that exhaust gases flowing through said protective cap are exposed to said sensing element; and
    at least one heating element affixed and thermally coupled to said protective cap and configured to heat the protective cap to a self-cleaning temperature for burning exhaust gas deposits formed thereon.

2. The exhaust gas sensor according to claim 1, wherein said heating element is arranged on the inner surface of said protective cap.

3. The exhaust gas sensor according to claim 1, wherein said heating element is arranged on the outer surface of said protective cap.

4. The exhaust gas sensor according to claim 1, further comprising at least one internal element arranged within said protective cap and supporting said at least one heating element.

5. The exhaust gas sensor according to claim 1, wherein said heating element comprises an electrical heater.

6. The sensor according to claim 5, wherein said electrical heater comprises at least one resistor element.

7. The exhaust gas sensor according to claim 6, wherein said heating element comprises a supporting layer having said at least one resistor fixed thereon.

8. The exhaust gas sensor according to claim 7, wherein said supporting layer comprises a steel member.

9. The exhaust gas sensor according to claim 7, wherein said supporting layer comprises a thermally conductive material.

10. The exhaust gas sensor according to claim 9, wherein said supporting layer comprises a steel member.

11. The exhaust gas sensor according to claim 1, wherein said heating element comprises a thick film heater.

12. The exhaust gas sensor according to claim 1, wherein said heating element is configured to heat said protective cap above a temperature greater than 600° C.

13. An internal combustion engine comprising an exhaust system having an exhaust pipe having a hole formed therethrough, wherein the exhaust gas sensor according to claim 1 is inserted into the hole such that the protective cap is exposed to exhaust gases flowing through the exhaust pipe.

14. A method for removing exhaust gas deposits from the protective cap of the exhaust gas sensor according to claim 1, wherein said method comprises activating said at least one heating element to heat the protective cap to a self-cleaning temperature for burning the exhaust gas deposits therefrom.

15. The method according to claim 14, further comprising heating the protective cap above a temperature greater than 600° C. with said heating element.

16. The method according to claim 14, further comprising preforming an engine cold start, and heating said protective cap by activating said heating element during the engine cold start.

17. The exhaust gas sensor according to claim 1, wherein the at least one electrical heating element is circumferentially affixed to an exterior surface of the protection cap.

18. A sensor for exhaust gases of an internal combustion engine, comprising:
    a sensor housing including a protective cap including an outer annular wall having a plurality of first openings formed therethrough and an inner annular wall supported within the outer annular wall and having a plurality of second openings formed therethrough;
    a sensing element enclosed in a sensor housing and extending within the inner annular wall such that exhaust gases flowing through said plurality of first and second openings in the protective cap are exposed to said sensing element; and
    an electrical heating element affixed and thermally coupled to said protective cap and configured to heat the protective cap to an elevated temperature for burning exhaust gas deposits formed thereon.

19. The sensor according to claim 18, wherein the electrical heating element is circumferentially affixed to an exterior surface of the outer annular wall.

20. The sensor according to claim 18, wherein the electrical heating element comprises a first resistor element affixed and thermally coupled to the outer annular wall and a second resistor element affixed and thermally coupled to the inner annular wall.

* * * * *